US009175280B2

(12) United States Patent
Gregory et al.

(10) Patent No.: US 9,175,280 B2
(45) Date of Patent: Nov. 3, 2015

(54) METHODS AND COMPOSITIONS FOR TREATING HEMOPHILIA B

(75) Inventors: Philip D. Gregory, Orinda, CA (US); Katherine A. High, Philadelphia, PA (US); Michael C. Holmes, Oakland, CA (US); Hojun Li, Ellicott City, MD (US)

(73) Assignees: Sangamo BioSciences, Inc., Richmond, CA (US); The Children's Hospital of Philadelphia, Philadephia, PA (US)

( * ) Notice: Subject to any disclaimer, the term of this patent is extended or adjusted under 35 U.S.C. 154(b) by 682 days.

(21) Appl. No.: 13/272,084

(22) Filed: Oct. 12, 2011

(65) Prior Publication Data

US 2012/0128635 A1 May 24, 2012

Related U.S. Application Data

(60) Provisional application No. 61/392,333, filed on Oct. 12, 2010.

(51) Int. Cl.
*C12P 21/06* (2006.01)
*A01N 63/00* (2006.01)
*C12N 5/00* (2006.01)
*A61K 48/00* (2006.01)
*C12N 9/64* (2006.01)
*A61K 31/7088* (2006.01)
*A61K 45/06* (2006.01)

(52) U.S. Cl.
CPC ............ *C12N 9/644* (2013.01); *A61K 31/7088* (2013.01); *A61K 45/06* (2013.01); *C12Y 304/21022* (2013.01)

(58) Field of Classification Search
CPC ........... C12N 9/644; C12Y 304/21022; A61K 45/06; A61K 31/7088
USPC ....................................................... 435/69.1
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,936,243 B2 | 8/2005 | Snyder et al. | |
| 6,979,539 B2 | 12/2005 | Cox, III et al. | |
| 7,013,219 B2 | 3/2006 | Cas et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,732,196 B2 | 6/2010 | Zhang et al. | |
| 2001/0051611 A1 | 12/2001 | Srivastava et al. | |
| 2003/0232410 A1 | 12/2003 | Liljedahl et al. | |
| 2005/0026157 A1* | 2/2005 | Baltimore et al. | ................. 435/6 |
| 2005/0064474 A1 | 3/2005 | Urnov et al. | |
| 2005/0208489 A1 | 9/2005 | Carroll et al. | |
| 2005/0245476 A1 | 11/2005 | Collingwood | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2007/0134796 A1 | 6/2007 | Holmes et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2008/0299580 A1 | 12/2008 | DeKelver et al. | |
| 2009/0068164 A1 | 3/2009 | Segal et al. | |

(Continued)

FOREIGN PATENT DOCUMENTS

GB  2338237  12/1999
WO  WO 95/19431 A1  7/1995

(Continued)

OTHER PUBLICATIONS

Maeder et al., 2008, Molecular Cell 31: 294-301.*
USPTO (STIC) Search (Sep. 25, 2013) pp. 1-18.*
Miller et al 2008, Nature Biotechnol. 25: 778-785.*
Aiuti, et al., "Gene Therapy for Immunodeficiency Due to Adenosine Deaminase Deficiency," *N. Engl. J. Med.* 360(5):447-458 (2009).
Beerli, et al., "Engineering Polydactyl Zinc-Finger Transcription Factors," *Nature Biotechnol.* 20:135-141 (2002).
Bitinate, et al., "Foki Dimerization is Required for DNA Cleavage," *PNAS USA* 95:10570-10575 (1998).

(Continued)

*Primary Examiner* — Christopher M Babic
*Assistant Examiner* — Kelaginamane T Hiriyanna
(74) *Attorney, Agent, or Firm* — Dahna S. Pasternak; Pasternak Patent Law

(57) ABSTRACT

Disclosed herein are methods and compositions for insertion of Factor IX (FIX) sequences into the genome of a cell for treating hemophilia B.

11 Claims, 7 Drawing Sheets

(56) References Cited

U.S. PATENT DOCUMENTS

| | | |
|---|---|---|
| 2009/0263900 A1 | 10/2009 | DeKelver et al. |
| 2009/0305346 A1 | 12/2009 | Miller |
| 2010/0218264 A1 | 8/2010 | Cui et al. |
| 2011/0027235 A1 | 2/2011 | Gregory et al. |
| 2011/0201055 A1 | 8/2011 | Doyon et al. |
| 2011/0301073 A1 | 12/2011 | Gregory et al. |

FOREIGN PATENT DOCUMENTS

| | | | |
|---|---|---|---|
| WO | WO 96/06166 A1 | | 2/1996 |
| WO | WO 98/37186 A1 | | 8/1998 |
| WO | WO 98/41240 A1 | | 9/1998 |
| WO | WO 98/53057 A1 | | 11/1998 |
| WO | WO 98/53058 A1 | | 11/1998 |
| WO | WO 98/53059 A1 | | 11/1998 |
| WO | WO 98/53060 A1 | | 11/1998 |
| WO | WO 98/54311 A1 | | 12/1998 |
| WO | WO 00/27878 A1 | | 5/2000 |
| WO | WO 01/60970 A2 | | 8/2001 |
| WO | WO 01/88197 A2 | | 11/2001 |
| WO | WO 02/16536 A1 | | 2/2002 |
| WO | WO 02/077227 A2 | | 10/2002 |
| WO | WO 02/099084 | * | 12/2002 |
| WO | WO 02/099084 A2 | | 12/2002 |
| WO | WO 03/016496 A2 | | 2/2003 |
| WO | WO 2005/100392 A2 | | 10/2005 |
| WO | WO 2006/094106 A2 | | 9/2006 |
| WO | WO 2007/014275 A2 | | 1/2007 |
| WO | WO 2009/009086 A2 | | 1/2009 |
| WO | WO 2009/042163 A2 | | 4/2009 |
| WO | WO 2010/065123 A1 | | 6/2010 |
| WO | WO 2010/079430 A1 | | 7/2010 |

OTHER PUBLICATIONS

Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From *Xanthomonas campestris pv. vesicatoria*," *Mol. Gen. Genet.* 218(1):127-136 (1989).
Cartier, et al., "Hematopoietic Stem Cell Gene Therapy With a Lentiviral Vector in X-Linked Adrenoleukodystrophy," *Science* 326(5954):818-823 (2009).
Choo, et al., "Advances in Zinc Finger Engineering," *Curr. Opin. Struct. Biol.* 10:411-416 (2000).
Christian, et al., "Targeting DNA Double-Strand Breaks With TAL Effector Nucleases," *Genetics* 186(2):757-761 (2010).
Gouble, et al., "Efficient in Toto Targeted Recombination in Mouse Liver by Meganuclease-Induced Double-Strand Break," *J. Gene Med.* 8(5):616-622 (2006).
Graham, et al., "Performance of AAV8 Vectors Expressing Human Factor IX From a Hepatic-Selective Promoter Following Intravenous Injection Into Rats," *Genet. Vaccines Ther.* 6:9 (2008).
Guo, et al., "Directed Evolution of an Enhanced and Highly Efficient FokI Cleavage Domain for Zinc Finger Nucleases," *J. Mol. Biol.* 400(1):96-107 (2010).
Guschin, et al., "A Rapid and General Assay for Monitoring Endogenous Gene Modification," *Meth. Mol. Biol.* 649:247-256 (2010).
Hanna, et al., "Treatment of Sickle Cell Anemia Mouse Model With IPS Cells Generated From Autologous Skin," *Science* 318(5858):1920-1923 (2007).
Heuer, et al., "Repeat Domain Diversity of AVRBS3-Like Genes in *Ralstonia solanacearum* Strains and Association With Host Preferences in the Field," *Appl. Environ. Microbiol.* 73(13):4379-4384 (2007).
High, et al., "Update on Progress and Hurdles in Novel Genetic Therapies for Hemophilia," *Hematol. Am. Soc. Hematol. Educ. Prog.* 466-72 (2007).
Isalan et al., "A Rapid, Generally Applicable Method to Engineer Zinc Fingers Illustrated by Targeting the HIV-1 Promoter," *Nat Biotechnol* 19:656-660 (2001).
Kay, et al., "A Bacterial Effector Acts as a Plant Transcription Factor and Induces a Cell Size Regulator," *Science* 318(5850):648-651 (2007).
Kim, et al., "Chimeric Restriction Endonuclease," *PNAS USA* 91:883-887 (1994).
Kim, et al., "Insertion and Deletion Mutants of FokI Restriction Endonuclease," *J. Biol. Chem.* 269:31978-31982 (1994).
Kim, et al., "Hybrid Restriction Enzymes: Zinc Finger Fusions to Fok I Cleavage Domain," *PNAS* 93(3):1156-1160 (1996).
Lee, et al., "A New Potent HFIX Plasmid for Hemophilia B Gene Therapy," *Pharm. Res.* 21(7):12291232 (2004).
Li, et al., "Functional Domains in Fok I Restriction Endonuclease," *PNAS USA* 89:4275-4279 (1992).
Li, et al., "Alteration of the Cleavage Distance of Fok I Restriction Endonuclease by Insertion Mutagenesis," *PNAS USA* 90:2764-2768 (1993).
Lin, et al., "A Coagulation Factor IX-Deficient Mouse Model for Human Hemophilia B," *Blood* 90(10):3962-3966 (1997).
Maguire, et al., "Safety and Efficacy of Gene Transfer for Leber's Congenital Amaurosis," *N. Engl. J Med.* 358(21):2240-2248 (2008).
Manno, et al., "Successful Transduction of Liver in Hemophilia by AAV-Factor IX and Limitations Imposed by the Host Immune Response," *Nat. Med.* 12:342-347 (2006).
Miao, et al., "Inclusion of the Hepatic Locus Control Region, an Intron, and Untranslated Region Increases and Stabilizes Hepatic Factor IX Gene Expression In Vivo but not In Vitro," *Mol. Ther.* 1(6):522-532 (2000).
Mitchell, et al., "A Reproducible and Well-Tolerated Method for 2/3 Partial Hepatectomy in Mice," *Nature Protocols* 3:1167-1170 (2008).
Moscou, et al., "A Simple Cipher Governs DNA Recognition by Tal Effectors," *Science* 326:1501 (2009).
Nakai, et al., "Extrachromosomal Recombinant Adeno-Associated Virus Vector Genomes are Primarily Responsible for Stable Liver Transduction In Vivo," *J. Virol.* 75(15):6969-6976.
Pabo, et al., "Design and Selection of Novel CYS2-HIS2 Zinc Finger Proteins," *Ann. Rev. Biochem.* 70:313-340 (2001).
Perez, et al., "Establishment of HIV-1 Resistance in CD4+ T Cells by Genome Editing Using Zinc-Finger Nucleases," *Nat. Biotechnol.* 26(7):808-816 (2008).
Schornack, et al., "Gene-for-Gene-Mediated Recognition of Nuclear-Targeted AVRBS3-Like Bacterial Effector Proteins," *J. Plant Physiol.* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Shen, et al., "Tissue-Specific Regulation of Human A1-Antitrypsin Gene Expression in Transgenic," *DNA* 8(2):101-108 (1989).
Thompson, et al., "Germ Line Origins of De Novo Mutations in Hemophilia B Families," *Hum Genet.* 94(3):299-302 (1994).
UNIPROT submission B4NMX5 (Sep. 23, 2008).
Yang, et al., "Purification, Cloning, and Characterization of the Cel I Nuclease," *Biochemistry* 39(13):3533-3541 (2000).
Li, et al., "In Vivo Genome Editing Restores Haemostasis in a Mouse Model of Haemophilia," *Nature* 475:217-221 (2011).

\* cited by examiner

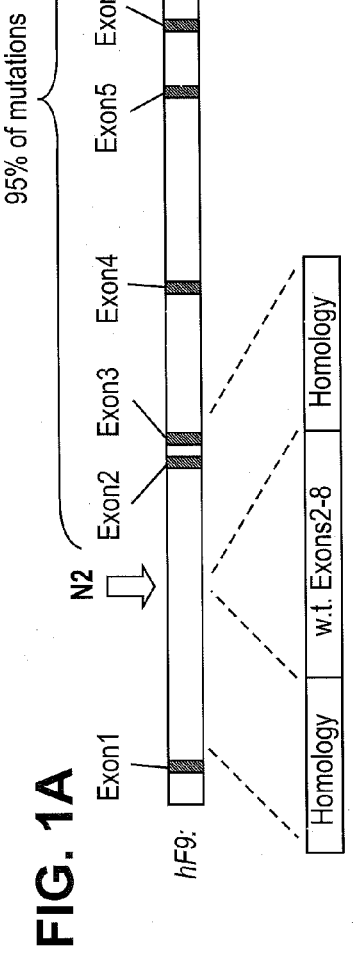

FIG. 2A
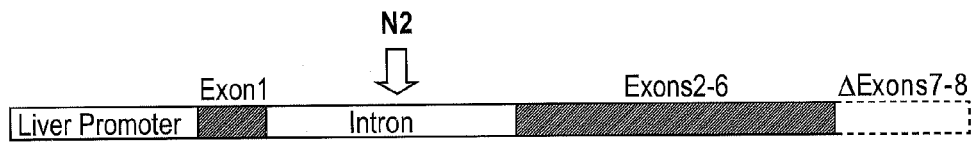
FIG. 2B
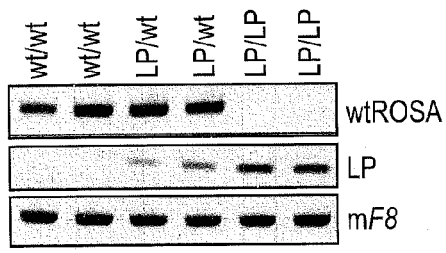
FIG. 2C
|  | wt/wt | LP/LP | LP/LP + AAV-hF.IX |
|---|---|---|---|
| Plasma hF.IX (ng/mL) | N.D. | N.D. | 31 |
FIG. 2D
FIG. 2E
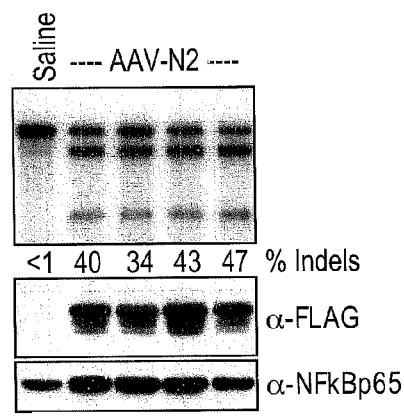

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tcggtgagtg atttgctgag                                           20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacctctcac ctggcctcat                                           20

<210> SEQ ID NO 3
<211> LENGTH: 28
<212> TYPE: DNA
<213> ORGANISM: Homo sapiens

<400> SEQUENCE: 3
tgacacagta cctggcacca tagttgta                                  28

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Gly Asp Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Asp Val Leu Ser Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Ser Asn Arg Ile Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Arg Ser Asp Asn Leu Ser Glu
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Asn Ala Thr Arg Ile Asn
1               5

<210> SEQ ID NO 9
<211> LENGTH: 28
<212> TYPE: DNA
<213> ORGANISM: Homo sapiens

<400> SEQUENCE: 9
gtactagggg tatggggata aaccagac                                             28

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Ser Leu Ser Val
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Gly His Leu Ser Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Asp His Leu Ser Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 13

His Ala Ser Thr Arg His Cys
1               5

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggccttattt acacaaaaag tctg                                           24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttgctctaa ctcctgttat ccatc                                          25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actgtcctct catgcgttgg                                                20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatgttggag gtggcatgg                                                 19

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catgtcttta atctacctcg atgg                                           24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 19
ctccctcgtg atctgcaact cc                                              22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctagtagctg acagtacc                                                   18

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaagaacaga agcctaatta tg                                              22

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acggtatcga taagcttgat atcgaattct ag                                   32

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cactgatctc catcaacata ctgc                                            24

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaataattct ttagttttag caa                                             23

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 25
accagcagtg ccatttcca                                                    19

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaattgacct ggtttggcat ct                                                22

<210> SEQ ID NO 27
<211> LENGTH: 9
<212> TYPE: PRT
<213> ORGANISM: Unknown
<220> FEATURE:
<223> OTHER INFORMATION: Description of Unknown: "LAGLIDADG"
      family peptide

<400> SEQUENCE: 27

Leu Ala Gly Leu Ile Asp Ala Asp Gly
1               5
```

METHODS AND COMPOSITIONS FOR TREATING HEMOPHILIA B

CROSS-REFERENCE TO RELATED APPLICATIONS

The present application claims the benefit of U.S. Provisional Application No. 61/392,333, filed Oct. 12, 2010, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of gene modification and treatment of hemophilia.

BACKGROUND

Hemophilia B is a genetic disorder of the blood-clotting system, characterized by bleeding into joints and soft tissues, and by excessive bleeding into any site experiencing trauma or undergoing surgery. While hemophilia B is clinically indistinguishable from hemophilia A, factor VIII (FVIII) is deficient or absent in hemophilia A and factor IX (FIX or F.IX) is deficient or absent in patients with hemophilia B. Factor IX encodes one of the serine proteases involved with the coagulation system, and it has been shown that restoration of even 3% of normal circulating levels of wild type Factor IX protein can prevent spontaneous bleeding.

Gene therapy, including liver-directed gene therapy protocols and direct intramuscular injection, involving the introduction of plasmid and other vectors (e.g., AAV) encoding a functional FIX protein have been described for treatment of hemophilia B. See, e.g., U.S. Pat. No. 6,936,243; Lee et al. (2004) Pharm. Res. 7:1229-1232; Graham et al. (2008) *Genet Vaccines Ther*. 3:6-9. However, in these protocols, the formation of inhibitory anti-factor IX (anti-FIX) antibodies and antibodies against the delivery vehicle remains a major complication of FIX protein replacement-based treatment for hemophilia B.

U.S. patent application Ser. No. 12/798,749 describes targeted integration of a functional FIX protein into isolated stem cells and treatment of hemophilia B by introduction of the FIX-producing stem cells into patients in need of treatment.

However, there remains a need for additional compositions and methods of treating hemophilia B in subjects with this disease.

SUMMARY

Disclosed herein are methods and compositions for targeted integration of a sequence encoding a functional FIX protein to treat hemophilia B. In particular, the methods involve administering nucleases that mediate targeted insertion of sequence encoding a functional FIX protein into the genome of cells for amelioration of the disease.

In one aspect, described herein is a DNA binding domain (e.g., zinc-finger protein (ZFP) or TALE protein) that binds to a target site in a region of interest (e.g., an Factor IX gene) in a genome, wherein the ZFP comprises one or more engineered zinc-finger binding domains and the TALE comprises one or more engineered TALE DNA-binding domains. In one embodiment, the DNA binding domain is a nuclease, e.g., a ZFP is a zinc-finger nuclease (ZFN) and a TALE is a TALE nuclease (TALEN) that cleaves a target genomic region of interest, wherein the ZFN or TALEN comprises one or more engineered DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in an endogenous FIX gene for example a zinc finger domain as shown in Table 1 (or a zinc finger domain that binds to a target site as shown in Table 1).

In another aspect, described herein is a polynucleotide encoding one or more ZFNs and/or TALENs described herein. The polynucleotide may be, for example, mRNA.

In another aspect, described herein is a ZFN and/or TALEN expression vector comprising a polynucleotide, encoding one or more ZFNs and/or TALENs described herein, operably linked to a promoter. In one embodiment, the expression vector is a viral vector. In one aspect, the viral vector exhibits tissue specific tropism.

In another aspect, described herein is a host cell comprising one or more ZFN and/or TALEN expression vectors. The host cell may be stably transformed or transiently transfected or a combination thereof with one or more ZFP or TALEN expression vectors. In one embodiment, the host cell is an embryonic stem cell. In other embodiments, the one or more ZFP and/or TALEN expression vectors express one or more ZFNs and/or TALENs in the host cell. In another embodiment, the host cell may further comprise an exogenous polynucleotide donor sequence. In any of the embodiments, described herein, the host cell can comprise a liver cell, a muscle cell, a stem cell or an embryo cell. The cells may be from any organism, for example human, non-human primate, mouse, rat, rabbit, cat, dog or other mammalian cells.

In another aspect, provided herein are methods for treating hemophilia B using nucleases to integrate a sequence encoding a FIX protein in a cell in a subject in need thereof. In certain embodiments, the FIX-encoding sequence is delivered using a viral vector, a non-viral vector (e.g., plasmid) and/or combinations thereof. In certain embodiments, the vector comprises an AAV vector, such as AAV8. In certain embodiments, the nucleases and/or FIX-encoding sequences are delivered via intravenous (e.g., intra-portal vein) administration into the liver of an intact animal.

In any of the methods described herein, the nuclease can be one or more zinc finger nucleases, one or more homing endonucleases (meganucleases) and/or one or more TAL-effector domain nucleases ("TALEN"). The nucleases (e.g., ZFN and/or TALEN) as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the ZFN binds to and/or cleaves an endogenous Factor IX gene (mutant or wild-type). In other embodiments, the ZFN and/or TALEN binds to and/or cleaves a safe-harbor gene (e.g., any gene which disruption of is not toxic or disruptive to the cell), for example a CCR5 gene, a PPP1R12c (also known as AAVS1) gene or a *Rosa* gene. See, e.g., U.S. Patent Publication Nos. 20080299580; 20080159996 and 201000218264.

Furthermore, any of the methods described herein may further comprise additional steps, including partial hepatectomy or treatment with secondary agents that enhance transduction and/or induce hepatic cells to undergo cell cycling. Examples of secondary agents include gamma irradiation, UV irradiation, tritiated nucleotides such as thymidine, cis-platinum, etoposide, hydroxyurea, aphidicolin, prednisolone, carbon tetrachloride and/or adenovirus.

The methods described herein can be practiced in vitro, ex vivo or in vivo. In certain embodiments, the compositions are introduced into a live, intact mammal. The mammal may be at any stage of development at the time of delivery, e.g., embryonic, fetal, neonatal, infantile, juvenile or adult. Additionally, targeted cells may be healthy or diseased. In certain embodiments, the compositions (e.g., polynucleotides encoding nuclease(s) and/or FIX-encoding sequences) are delivered to the liver of a live animal, for example via intraportal injection. In other embodiments, one or more of the compositions are delivered intravenously (other than the intraportal vein, for example tail vein injection), intra-arterially, intraperitoneally, into liver parenchyma (e.g., via injection), into the hepatic artery (e.g., via injection), and/or through the biliary tree (e.g., via injection)

For targeting the compositions to a particular type of cell, e.g., hepatocytes, one or more of the administered compositions may be associated with a homing agent that binds specifically to a surface receptor of the cell. For example, the vector may be conjugated to a ligand (e.g., galactose) for which certain hepatic system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

The target cells may be human cells, or cells of other mammals (including veterinary animals), especially nonhuman primates and mammals of the orders Rodenta (mice, rats, hamsters), Lagomorpha (rabbits), Carnivora (cats, dogs), and Arteriodactyla (cows, pigs, sheep, goats, horses). In some aspects, the target cells comprise a tissue (e.g. liver). In some aspects, the target cell is a stem cell (e.g., an embryonic stem cell, an induced pluripotent stem cell, a hepatic stem cell, etc.) or animal embryo by any of the methods described herein, and then the embryo is implanted such that a live animal is born. The animal is then raised to sexual maturity and allowed to produce offspring wherein at least some of the offspring comprise the genomic modification.

These and other aspects will be readily apparent to the skilled artisan in light of disclosure as a whole. Thus, the disclosure encompasses the following embodiments:

1. A protein comprising an engineered zinc finger protein DNA-binding domain, wherein the DNA-binding domain comprises four or five zinc finger recognition regions ordered F1 to F4 or F1 to F5 from N-terminus to C-terminus, and wherein
   (i) when the DNA-binding domain comprises five zinc finger recognition regions, F1 to F5 comprise the following amino acid sequences:

F1: QSGDLTR  (SEQ ID NO: 4)

F2: RSDVLSE  (SEQ ID NO: 5)

F3: DRSNRIK  (SEQ ID NO: 6)

F4: RSDNLSE  (SEQ ID NO: 7)

F5: QNATRIN;  (SEQ ID NO: 8)

(ii) when the DNA-binding domain comprises four zinc finger recognition regions, F1 to F4 comprise the following amino acid sequences:

F1: RSDSLSV  (SEQ ID NO: 10)

F2: TSGHLSR  (SEQ ID NO: 11)

F3: RSDHLSQ  (SEQ ID NO: 12)

F4: HASTRHC.  (SEQ ID NO: 13)

2. The protein according to 1, further comprising a cleavage domain or cleavage half-domain.

3. The protein of 2, wherein the cleavage half-domain is a wild-type or engineered FokI cleavage half-domain.

4. A polynucleotide encoding the protein of any of 1 to 3.

5. A gene delivery vector comprising a polynucleotide of 4.

6. An isolated cell comprising the protein of any of 1 to 3 or the polynucleotide of 4.

7. An isolated cell comprising the protein of any of the 1 to 3 or the polynucleotide of 4.

8. A method for treating hemophilia B in a subject, the method comprising inserting (e.g., via targeted integration) a sequence encoding a functional Factor IX (FIX) protein into the genome of a cell using at least one nuclease, wherein the subject comprises the cell.

9. The method of 8, wherein the sequence is integrated into an endogenous gene.

10. The method of 9, wherein the endogenous gene is selected from the group consisting of a FIX gene and a safe-harbor gene.

11. The method of any of 8 to 10, wherein the sequence and/or the nuclease is delivered to the cell using a vector selected from the group consisting of a viral vector, a non-viral vector and combinations thereof.

12. The method of any of 8 to 11, wherein the cell is a hepatic cell and the sequence is delivered to the cell by intravenous administration (e.g., into the liver) of an intact animal.

13. The method of any of 8 to 12, wherein the at least one nuclease is a zinc finger nuclease, a TALEN or a homing endonuclease.

14. The method of any of 8 to 13, further comprising the step of performing a partial hepatectomy on the subject.

15. The method of any of 8 to 14, further comprising the step of treating the subject with at least one secondary agent.

16. The method of 15, wherein the secondary agent is selected from the group consisting of gamma irradiation, UV irradiation, tritiated nucleotides, cis-platinum, prednisolone, carbon tetrachloride, etoposide, hydroxyurea, aphidicolin, adenovirus and combinations thereof.

17. The method of any of 8 to 16, wherein the cell is an isolated cell and the method further comprises administering the isolated cell to the subject.

18. The method of any of 8 to 17, wherein the subject is selected from the group consisting of an embryo, a fetus, a neonate, an infant, a juvenile or an adult.

19. The method of any of 8 to 18, further comprising associating the sequence with a homing agent that binds specifically to a surface receptor of the cell.

20. The method of 19, wherein the homing agent comprises galactose or a hybrid of an AAV coat protein and galactose.

21. The method of any of 8 to 20, further comprising associating a polynucleotide encoding the at least one nuclease with a homing agent that binds specifically to a surface receptor of the cell.

22. The method of 21, wherein the homing agent comprises galactose or a hybrid of an AAV coat protein and galactose.

23. The method of any of 8 to 22, wherein the cell is selected from the group consisting of a human cell, a nonhuman primate cell, a Rodenta cell, a Lagomorpha cell, a Carnivora cell and an Arteriodactyla cell.

24. The method of any of 8 to 22, wherein the target cell is a stem cell.

25. The method of 24, wherein the stem cell is an embryonic stem cell, an induced pluripotent stem cell, a hematopoietic stem cell, a hepatocyte or a hepatic stem cell.

26. The method of any of 8 to 25, wherein the nuclease comprises a zinc finger nuclease according to any of 1 to 3, a polynucleotide according to 4 or a gene delivery vehicle according to 5.

BRIEF DESCRIPTION OF THE DRAWINGS

FIG. 1, panels A-E, show N2 ZFNs efficiently cleave the gene encoding Factor IX (F9) intron 1 and induce homologous recombination in human cells. FIG. 1A depicts a schematic depicting the target of the N2 ZFN pair in intron 1 of the human F9 gene. FIG. 1B depicts the bi-cistronic FLAG-tagged ZFN expression plasmid. FIG. 1C shows a gel with the results of a Surveyor® mismatch assay (Transgenomics, "Cel-I") following transfection of the N2 ZFN expression plasmid into K562 cells. The assay demonstrates the result of NHEJ repair of a DSB induced by the N2 ZFNs at intron 1 of the hF9 gene at day 3 post-transfection. ZFN expression was confirmed by α-FLAG immunoblotting and protein loading was assessed using an α-NFkB p65 antibody. FIG. 1D shows a schematic of the targeted integration (TI) assay detailing the time-course of ZFN-mediated targeting of a NheI restriction site tag into the hF9 gene. FIG. 1E shows a gel depicting the results of a RFLP assay following co-transfection of ZFN expression plasmid with increasing amounts of NheI tag donor plasmid (0-4 μg). The data show increasing levels of gene targeting at days 3 and 10 post-transfection, whereas transfection of the NheI tag donor alone (4 μg, '(−) ZFN') does not result in detectable gene targeting. Black arrows denote NheI-sensitive cleavage products resulting from TI at both day 3 and 10. TI PCR performed with PCR using $^{32}$P-labeled nucleotides and the band intensity was quantified by phosphorimager. ZFN expression confirmed by α-FLAG immunoblotting and protein loading was assessed using an α-NFkB p65 antibody.

FIG. 2, panels A-E, show AAV-mediated delivery of N2 ZFNs to mice including an N2 "landing pad" (LP) results in efficient cleavage of the Landing Pad (LP) intron 1. FIG. 2A depicts a diagram showing how the N2 ZFNs target intron 1 of a human F9 mini-gene (LP), which mimics a published HB-causing mutation (Thompson et al, (1994) *Hum. Genet.* 94: 299-302). FIG. 2B shows the gel from a PCR analysis demonstrating the LP construct has been knocked in to the mouse ROSA26 locus. FIG. 2C shows the results of an ELISA to detect circulating plasma hFIX. The data shows that LP mice do not have circulating plasma hFIX, as measured using a hFIX-specific ELISA, unless the mice are injected with a viral vector expressing hFIX (1e10 viral genomes (v.g.) AAV-hFIX injected via tail vein). FIG. 2D depicts a bi-cistronic AAV8-N2 ZFN expression vector with expression controlled by the ApoE enhancer and human alpha1-antitrypsin promoter. FIG. 2E shows the results of a Cel-I assay performed following tail vein injection of 1e11 v.g. AAV-N2 expression vector into LP mice that results in cleavage of the LP intron 1 in liver DNA at day 7 post-injection. Cel-1 assay was performed with a PCR amplicon using $^{32}$P-labeled nucleotides and the band intensity quantified by phosphorimager. ZFN expression is confirmed by α-FLAG immunoblotting of whole liver lysates and protein loading was assessed using an α-NFkB p65 antibody.

FIG. 3, panels A and B, show N2 ZFNs promote AAV-mediated targeting of wild-type F9 exons 2-8 to Landing Pad intron 1 in vivo.

FIG. 4, panels A-F, show in vivo hepatic gene correction results in therapeutic levels of circulating FIX.

FIG. 5, panels A and B, show in vivo hepatic gene correction results in the expression of therapeutic levels of circulating FIX.

DETAILED DESCRIPTION

Figure 3A:
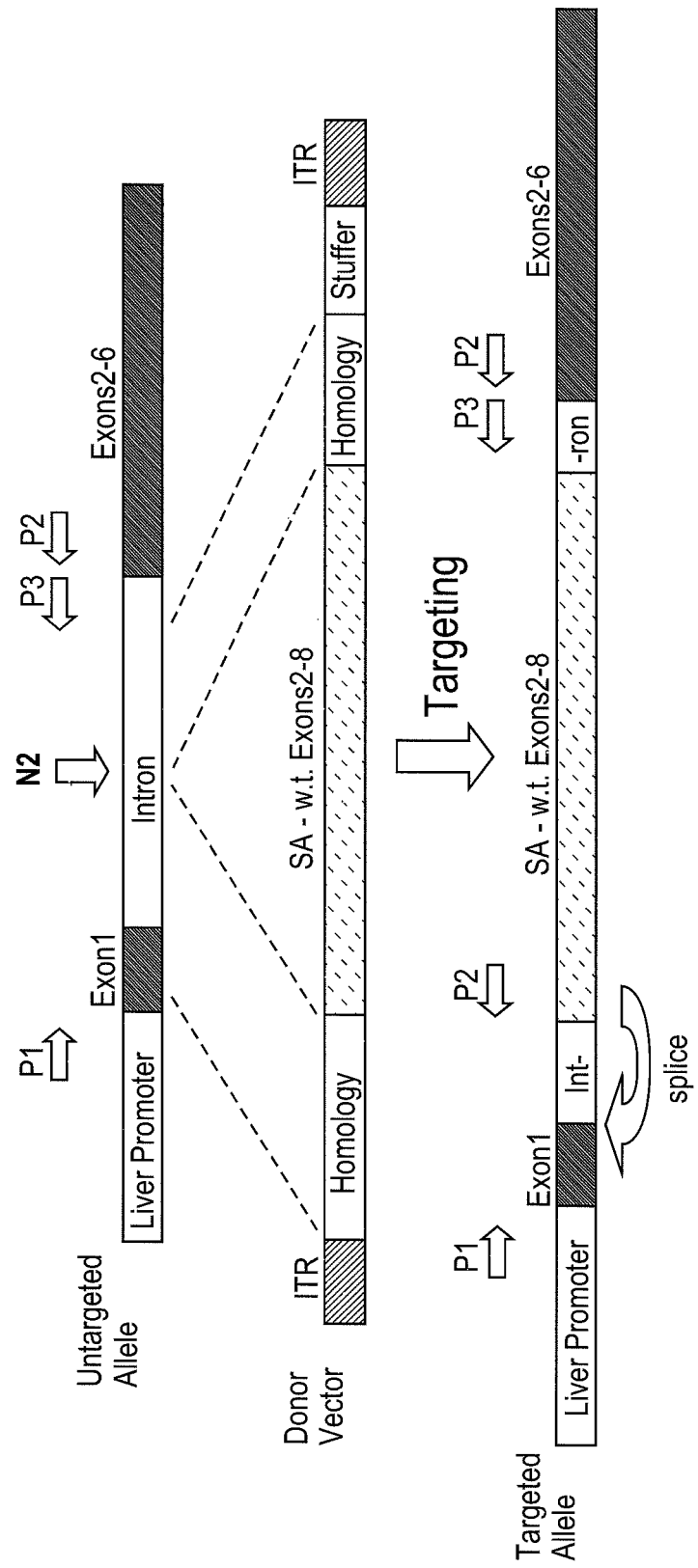
FIG. 3A shows a schematic of how the LP gene mutation can be bypassed by TI of hF9 exons 2-8 into intron 1. Targeted and untargeted LP alleles can be differentiated through PCR using primers P1, P2, and P3.

Disclosed herein are compositions and methods for treating patients with hemophilia B. In particular, nuclease-mediated targeted integration is used to insert a sequence encoding FIX into the genome of one or more cells of the subject (in vivo or ex vivo), such that the cells produce FIX in vivo. In certain embodiments, the methods further comprise inducing cells of the subject, particularly liver cells, to proliferate (enter the cell cycle), for example, by partial hepatectomy and/or by administration of one or more compounds that induce hepatic cells to undergo cell cycling. Subjects include but are not limited to humans, non-human primates, veterinary animals such as cats, dogs, rabbits, rats, mice, guinea pigs, cows, pigs, horses, goats and the like.

The methods described herein result in treatment of hemophilia B. Unlike previously described methods in in vivo models of nuclease-mediated gene correction using meganucleases (see Gouble et al, (2006) *J Gene Med*. May; 8(5):616-22) little or no toxicity is observed following nuclease-mediated integration of a FIX gene in the animal models. In addition, the methods and compositions of the invention are functional in neonates and adult animals, leading to functional activity of the inserted Factor IX transgene.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P.M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. application Ser. No. 13/068,735.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to upregulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci in mammalian cells are the AAVS1 gene (see U.S. Publication No. 20080299580), the CCR5 gene (see U.S. Publication No. 20080159996), and/or the *Rosa* locus (see WO 2010/065123).

Nucleases

Described herein are compositions, particularly nucleases, that are useful in integration of a sequence encoding a functional FIX protein in the genome of a cell from a subject with hemophilia B. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO:27)family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. patent application Ser. No. 13/068,735, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet.* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. See, e.g., U.S. patent application Ser. No. 13/068,735, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. patent application Ser. No. 13/068,735; Christian et al ((2010)<*Genetics* epub 10.1534/genetics.110.120717).

In certain embodiments, the DNA binding domain comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Thus, the nuclease comprises a DNA-binding domain in that specifically binds to a target site in any gene into which it is desired to insert a sequence encoding a FIX protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275. Likewise, TALE DNA-binding domains have been fused to nuclease domains to create TALENs. See, e.g., U.S. application Ser. No. 13/068,735.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res*. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type H is (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type H is (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) *J. Mol. Biol*. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice, for example in an endogenous FIX gene or an endogenous or inserted safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Provisional Application Nos. 61/395,836 and 61/401,429, filed May 17, 2010 and Aug. 21, 2010, respectively.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. application Ser. No. 13/066,735.

For treatment of hemophilia B via targeted insertion of a sequence encoding a functional FIX protein, any desired site of insertion in the genome of the subject is cleaved with a nuclease, which stimulates targeted insertion of the donor polynucleotide carrying the FIX-encoding sequence. DNA-binding domains of the nucleases may be targeted to any desired site in the genome.

In certain embodiments, the DNA-binding domain of the nuclease is targeted to the endogenous FIX (F9) gene, as described for example in U.S. patent application Ser. No. 12/798,749. The target sites may be anywhere in the coding sequence or upstream or downstream of the coding sequence. In certain embodiments, the target site(s) is (are) near the 3' end of the coding sequence.

In other embodiments, the nuclease (DNA-binding domain component) is targeted to a "safe harbor" locus, which includes, by way of example only, the AAVS1 gene (see U.S. Publication No. 20080299580), the CCR5 gene (see U.S. Publication No. 20080159996), and/or the Rosa locus (see WO 2010/065123).

Donor Sequences

For treating hemophilia, the donor sequence comprises a sequence encoding a functional FIX protein, or part thereof, to result in a sequence encoding and expressing a functional FIX protein following donor integration. The donor molecule may be inserted into an endogenous gene such that all, some or none of the endogenous gene is expressed. For example, a transgene comprising function FIX sequences as described herein may be inserted into an endogenous FIX locus such that some or none of the endogenous FIX is expressed with the FIX transgene (e.g., the donor may correct a mutation such that the wild-type endogenous sequences are expressed). In other embodiments, the FIX transgene is integrated into any endogenous locus, for example a safe-harbor locus (endogenous or inserted). See, e.g., US patent publications 20080299580; 20080159996 and 201000218264.

The FIX donor sequence can be introduced into the cell prior to, concurrently with, or subsequent to, expression of the fusion protein(s). The FIX donor polynucleotide typically contains sufficient homology to a genomic sequence to support homologous recombination (or homology-directed repair) between it and the genomic sequence to which it bears homology. See, e.g., U.S. Patent Publication Nos. 2005/0064474; 2007/0134796 and 2009/0263900. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The FIX donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

The FIX donor is generally inserted so that its expression is driven by the endogenous promoter at the integration site (e.g., the endogenous FIX promoter when the donor is integrated into the patient's defective FIX (F9) locus). However, it will be apparent that the donor may comprise a promoter and/or enhancer, for example a constitutive promoter or an inducible or tissue specific (e.g., liver specific) promoter that drives expression of the function FIX protein upon integration.

The FIX donor sequence can be integrated specifically into any target site of choice, thereby eliminating the issues associated with random integration in traditional gene therapy. In certain embodiments, the donor sequence is integrated into the endogenous FIX locus to correct the deficiency in the patient with hemophilia B. In other embodiments, the FIX donor sequence is integrated into a safe harbor locus, for example CCR5 locus, AAVS1 locus or the like.

Furthermore, although not required for expression, exogenous sequences may also contain transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech*. 25(12):1444-1454 as well as general gene delivery references such as Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946, 787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res*. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol*. 66:2731-2739 (1992); Johann et al., *J. Virol*. 66:1635-1640 (1992); Sommerfelt et al., *Virol*. 176:58-59 (1990); Wilson et al., *J. Virol*. 63:2374-2378 (1989); Miller et al., *J. Virol*. 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest*. 94:1351 (1994). Construction of recombinant AAV vectors are described in a number of publications, including U.S. Pat. No. 5,173,414; Tratschin et al., *Mol. Cell. Biol*. 5:3251-3260 (1985); Tratschin, et al., *Mol. Cell. Biol*. 4:2072-2081 (1984); Hermonat & Muzyczka, PNAS 81:6466-6470 (1984); and Samulski et al., *J. Virol*. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med*. 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother*. 44(1):10-20 (1997); Dranoff et al., *Hum. Gene Ther*. 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and $\psi$12 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a. receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or FIX-encoding) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of Hemophilia B, via nuclease-mediated integration of FIX-encoding sequence. The compositions are administered to a human patient in an amount effective to obtain the desired concentration of the therapeutic FIX polypeptide in the serum, the liver or the target cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics*, 6:335-341.

The effective amount of nuclease(s) and FIX donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.*, 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains or TALENs.

EXAMPLES

Example 1

Fix Specific ZFNs and their Use for Targeted Integration

Gene transfer as a strategy for treating genetic disease has been successfully carried out in a variety of animal models of disease, and more recently, in human applications (see, e.g., Aiuti et al, (2009) *N. Engl. J. Med.* 360: 447-458; Maguire et al, (2009) *N. Engl. J. Med.* 358: 2240-2248; Cartier et al, (2009) *Science* 326: 818-823). Gene targeting has been used to correct ex vivo cultured ES-like induced pluripotent stem cells (Hanna et al, (2007) *Science* 318: 1920-1923), but the majority of genetic diseases affect organ systems where ex vivo manipulation is currently not feasible. One such organ is the liver, the major site of plasma protein synthesis, including the blood coagulation factors. A model genetic disease for liver gene therapy is hemophilia B, caused by deficiency of blood coagulation factor IX (FIX), encoded by the F9 gene. Targeted integration (TI) of the wild type exons 2-8 into F9 intron 1 would allow for splicing of wild type coding sequence with exon 1 (FIG. 1A), leading to expression of wild type FIX and rescue of the defect caused by most F9 mutations. We thus sought to investigate whether ZFNs combined with a targeting vector carrying the wild type F9 exons 2-8 could induce gene targeting in vivo, to correct a mutated F9 gene in situ within the genome of hepatocytes.

ZFN pairs targeting the human F9 intron 1 were used to test the ability of these ZFNs to induce DSBs at a specific target site. The Cel-I assay (Surveyor™, Transgenomics. Perez et al, (2008) *Nat. Biotechnol.* 26: 808-816 and Guschin et al, (2010) *Methods Mol. Biol.* 649:247-56), was used where PCR-amplification of the target site was followed by quantification of insertions and deletions (indels) using the mismatch detecting enzyme Cel-I (Yang et al, (2000) *Biochemistry* 39, 3533-3541) which provides a lower-limit estimate of DSB frequency. Three days following transfection of the ZFN expression vector, genomic DNA was isolated from K562 cells using the DNeasy kit (Qiagen). Primers for the Cel-I analysis of hF9 intron 1 were N2 For (TCGGTGAGTGATTTGCTGAG, SEQ ID NO:1) and N2 Rev (AACCTCTCACCTGGCCTCAT, SEQ ID NO:2). The highest activity ZFN pair, designated N2, targeting intron 1 of the hF9 gene, shown below in Table 1 (also see United States Publication No. 20110027235):

TABLE 1 hFactor9-specific ZFN pair N2

| | ZFN Name | | | | |
|---|---|---|---|---|---|
| Target site | F1 | F2 | F3 | F4 | F5 |
| SBS#9802<br>tgACACAGTACCTGGCAccatagttgta<br>(SEQ ID NO: 3) | QSGDLTR<br>(SEQ ID<br>NO: 4) | RSDVLSE<br>(SEQ ID<br>NO: 5) | DRSNRIK<br>(SEQ ID<br>NO: 6) | RSDNLSE<br>(SEQ ID<br>NO: 7) | QNATRIN<br>(SEQ ID<br>NO: 8) |
| SBS#11004<br>gtACTAGGGGTATGgggataaaccagac<br>(SEQ ID NO: 9) | RSDSLSV<br>(SEQ ID<br>NO: 10) | TSGHLSR<br>(SEQ ID<br>NO: 11) | RSDHLSQ<br>(SEQ ID<br>NO: 12) | HASTRHC<br>(SEQ ID<br>NO: 13) | N/A |

The N2 ZFN expression plasmid for cell culture transfection was constructed by inserting a 2A linker from the Thosea asigna virus between the coding sequences for both ZFNs, and inserting this cassette downstream of a CMV promoter.

Upon transfection of the N2 ZFN pair into human K562 cells, we found that 30% of N2 target site alleles were cleaved (FIG. 1C). To test the ability of the N2 ZFNs to stimulate homologous recombination by inducing DSBs, we co-transfected the N2 ZFNs into K562 cells with a targeting vector that inserts a NheI restriction site (FIG. 1D). The NheI donor plasmid was constructed by amplifying the left and right arms of homology from K562 genomic DNA by PCR. A short sequence containing a NheI restriction site was subsequently introduced between the left and right arms of homology. We found that at days 3 and 10 post-transfection, 14% and 12%, respectively, of alleles were sensitive to NheI digestion (FIG. 1E), indicative of efficient rates of targeted integration (TI) through homologous recombination.

Example 2

In Vivo Murine Model of Human Hemophilia

The N2 target site is present in hF9 intron 1, but absent from the murine F9 gene. Thus, to test the N2 ZFNs in vivo we generated a humanized mouse model of hemophilia B (HB). We constructed an hF9 mini-gene (FIG. 2A) under control of a liver-specific promoter (Shen et al, (1989) *DNA* 8: 101-108 and Miao et al, (2000) *Mol. Ther*. 1: 522-532). Primers for TI of hF9 intron 1 were N2 TI For (GGCCTTATTTACA-CAAAAAGTCTG, SEQ ID NO:14) and N2 TI Rev (TTTGCTCTAACTCCTGTTATCCATC, SEQ ID NO:15).

Intron 1 of this construct contains the human N2 target site (Landing Pad, LP). The remainder of the F9 sequence in the LP construct mimics a previously identified nonsense mutation (Y155stop) (Thompson et al, (1989) *Hum. Genet.* 94: 299-302) in which a premature stop codon prior to exons encoding the FIX catalytic domain results in an absence of circulating FIX protein. The LP construct was constructed by gene synthesis (Genscript) and ligated into the pUC57 plasmid. The LP construct was then excised by SwaI digestion and ligated into the SwaI site of a proprietary plasmid between FLP recombinase sites compatible for recombinase-mediated cassette exchange (RCME) (Taconic-Artemis) to create the LP KI plasmid. The LP KI plasmid and a FLP recombinase expression plasmid (Taconic-Artemis) were transfected into B6S6F1 embryonic stem (ES) cells containing FLP recombinase sites compatible for RCME at the ROSA26 locus (Zambrowicz et al, (1997) *Proc Natl Acad Sci* 94: 3789-3794). Correctly targeted B6S6F1-LP ES cell clones were identified by Southern blot and injected into B6D2F1 blastocysts. Pure ES cell derived B6S6F1-LP mice (G0) were delivered by natural birth, and chimeric pups were back-crossed with wild type C57BL/6J mice (Jackson Laboratories) for 5 generations (in vivo cleavage experiments) or 7-10 generations (in vivo TI experiments).

LP mice were genotyped using primers LP Oligo 1 (ACTGTCCTCTCATGCGTTGG, SEQ ID NO:16), LP Oligo 2 (GATGTTGGAGGTGGCATGG, SEQ ID NO:17), wtROSA Oligo 1 (CATGTCTTTAATCTACCTCGATGG, SEQ ID NO:18), and wtROSA Oligo2 (CTCCCTCGTGATCTG-CAACTCC, SEQ ID NO:19) (FIG. 2B). We also crossed LP mice with an existing mouse model that has a deletion of the murine F9 gene (Lin et al, (1997) *Blood* 90, 3962-3966) to generate LP/HB mice in which we could test N2 ZFN activity in vivo.

HB mice have been back-crossed with C57BL/6J mice (Jackson Laboratories) for >10 generations. C57BL/6J mice (Jackson Laboratories) were used for LP-negative TI experiments. As expected, LP mice did not have detectable circulating hFIX (FIG. 2c). Quantification of plasma hFIX was performed using an hFIX ELISA kit (Affinity Biologicals), with a standard curve from pooled normal human plasma (Trinity Biotech). All values below the last value of the standard curve (15 ng/mL) were arbitrarily given the value of 15 ng/mL, which is the limit of detection. Plasma for hFIX ELISA was obtained by retro-orbital bleeding into heparinized capillary tubes.

Example 3

Targeted Delivery of FIX-Specific ZFNs In Vivo

To deliver the N2 ZFNs to the liver, the normal site of FIX production, we generated a hepatotropic adeno associated virus vector, serotype 8 (AAV8-N2) expressing the N2 ZFNs from a liver-specific enhancer and promoter (Shen et al, ibid and Miao et al, ibid) (FIG. 2D).

To test the cleavage activity of the N2 ZFNs in vivo we performed tail vein injections into LP mice using 1e11 v.g. AAV8-N2 expression vector and isolated liver DNA at day 7 post-injection. PCR-amplification of the LP and Cel-I assay demonstrated that 34-47% of LP alleles had been cleaved (FIG. 2E). Primers for Cel-I of the LP construct were LP N2 For (CTAGTAGCTGACAGTACC, SEQ ID NO:20) and LP N2 Rev (GAAGAACAGAAGCCTAATTATG, SEQ ID NO:21).

Example 4

In Vivo Co-Delivery of a Donor Nucleic Acid and Fix-Specific ZFNs

Insertion of the wild-type exons 2-8, preceded by a splice acceptor (SA), into intron 1 of the LP construct allows for splicing of wild type coding sequence with exon 1 (FIG. 3A). To correct the mutated F9 gene in situ in LP mice, we generated an AAV donor template vector (AAV-Donor) for gene targeting, with arms of homology, flanking a "SA—wild-type hF9 exons 2-8" cassette (FIG. 3A). The donor vector production plasmids were constructed by amplifying the left and right arms of homology from LP mouse genomic DNA by PCR. The "splice acceptor—exons 2-8 coding sequence—bovine growth hormone polyA signal" cassette was obtained by PCR amplification from the pAAV-hFIX16 plasmid (Manno et al, (2006) *Nat. Med.* 12: 342-347) and ligated between the left and right arms of homology. Since HR is favored during the S/G2 phases of the cell cycle, we delivered the N2 and Donor vectors to neonatal mice, where rapidly proliferating hepatocytes enter S/G2 during cell cycle progression.

We injected LP/HB mice at day 2 of life with either AAV-N2 (5e10 v.g) alone (n=1), AAV-N2 (5e10 v.g)+AAV-Donor (2.5e11 v.g) (n=5), or AAV-Mock (5e10 v.g)+AAV-Donor (2.5e11 v.g) (n=5). In the Mock vector, the N2 ZFNs have been replaced by renilla luciferase.

At week 10 of life, we sacrificed mice and isolated liver DNA to assay for TI of the donor using two separate PCR strategies. The first strategy uses primers that generate a smaller amplicon for a targeted LP allele and a larger amplicon for an untargeted LP allele (FIG. 3a, primers P1/P2). The second strategy involves using primers that generate a larger amplicon for a targeted LP allele and a smaller amplicon for an untargeted LP allele (FIG. 3A, primers P1/P3). Primers for TI of the LP construct were P1 (ACGGTATCGATAAGCT-TGATATCGAATTCTAG, SEQ ID NO:22), P2 (CACT-GATCTCCATCAACATACTGC, SEQ ID NO:23), and P3 (GAATAATTCTTTAGTTTTAGCAA, SEQ ID NO:24).

Figure 3B:
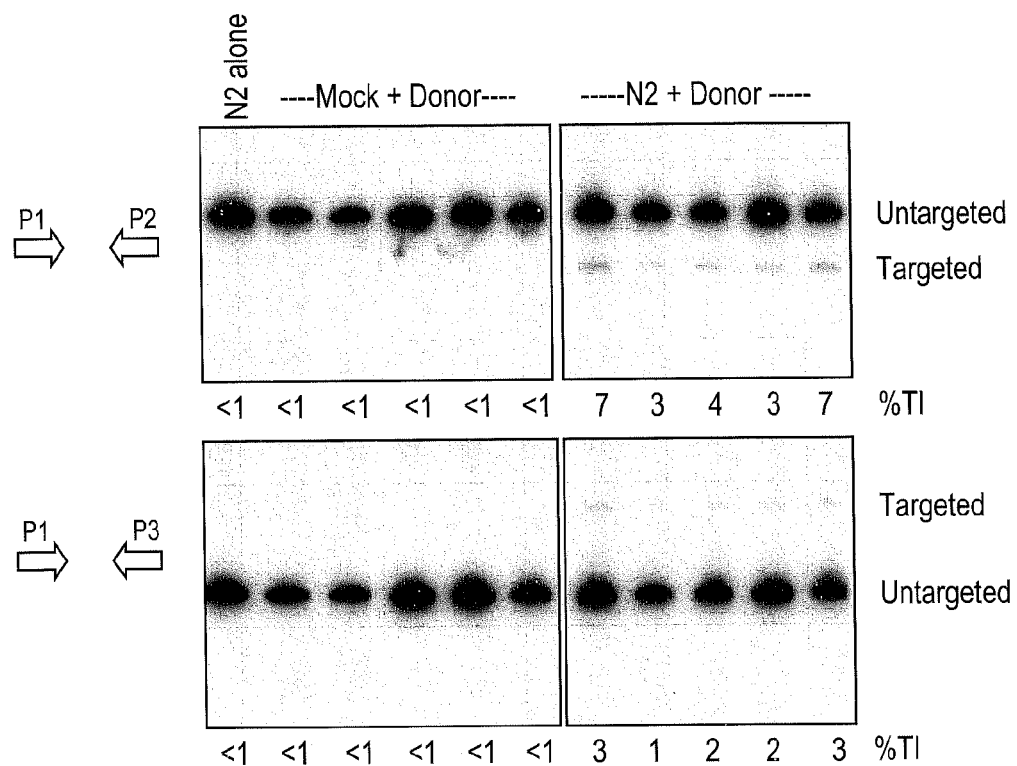
FIG. 3B depicts a gel of a PCR analysis with primer pairs P1/P2 and P1/P3 demonstrating successful gene targeting upon I.P. co-injection of 5e10 v.g. AAV8-N2 and 2.5e11 v.g. AAV8-Donor in LP/HB mice at day 2 of life, but not with injection of 5e10 v.g. AAV8-N2 alone, or co-injection of 5e10 v.g. AAV8-Mock and 2.5e11 v.g. AAV8-Donor. PCR was performed using $^{32}$P-labeled nucleotides, allowing for quantification of product band intensity by phosphorimager to evaluate targeting frequency. In targeted samples, primers P1 and P2 will generate a smaller product indicating successful amplification of the targeted wild-type F9 exons 2-8, while primers P1 and P3 will generate a larger product than the untargeted allele.

When we performed both PCR analyses, we found evidence of TI only in mice receiving N2+Donor (FIG. 3B). Quantification of band intensities suggested 1-7% TI frequency (FIG. 3B).

To determine if genomic correction results in production of circulating hFIX, we injected LP mice at day 2 of life with AAV-N2 alone (n=7), AAV-Mock+AAV-Donor (n=6), or AAV-N2+AAV-Donor (n=7) (same vector doses as above). Plasma hFIX levels for mice receiving N2 alone or Mock+Donor averaged less than 15 ng/mL (the lower limit of detection of the assay), while mice receiving N2+Donor averaged 116-121 ng/mL (corresponding to 2-3% of normal) (FIG. 4A), significantly greater than mice receiving N2 alone and Mock+Donor (p≤0.006 at all time points, 2-tailed T-test).

Figure 4B:
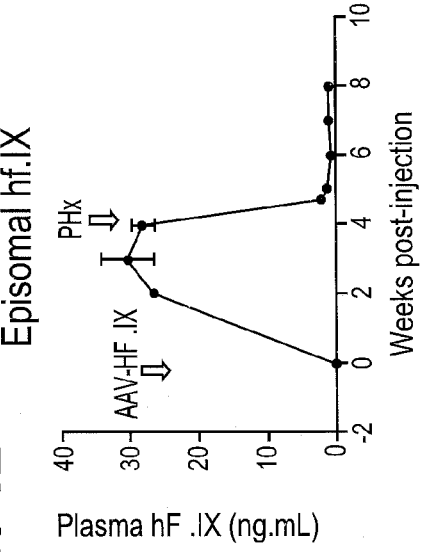
FIG. 4B is a graph showing plasma hFIX levels in wild-type mice (n=5) following tail vein injection of 1e12 v.g. AAV-hFIX (predominantly episomal) with subsequent PHx. Error bars denote standard error.
Figure 4D:
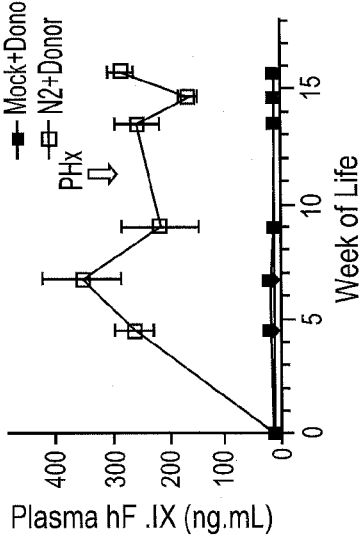
FIG. 4D is a graph of plasma hFIX levels in LP/HB mice following intraperitoneal (I.P.) injection at day 2 of life with either 5e10 v.g. AAV-N2 alone (n=10 pre-PHx, n=1 post-PHx), 5e10 v.g. AAV-N2 and 2.5e11 v.g. AAV-Donor (n=9 pre-PHx, n=5 post-PHx), or 5e10 v.g. AAV-Mock and 2.5e11 v.g. AAV-Donor (n=9 pre-PHx, n=3 post-PHx). Error bars denote standard error.
Figure 4A:
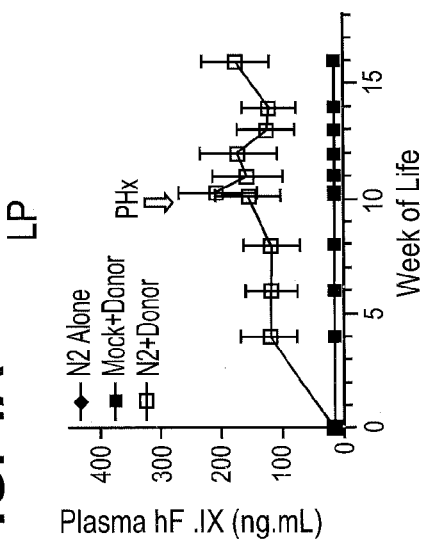
FIG. 4A is a graph showing the plasma hFIX levels in LP mice following I.P. injection at day 2 of life with either 5e10 v.g. AAV-N2 alone (n=7 pre- and post-partial hepatectomy (PHx)), 5e10 v.g. AAV-N2 and 2.5e11 v.g. AAV-Donor (n=7 pre- and post-PHx), or 5e10 v.g. AAV-Mock and 2.5e11 v.g. AAV-Donor (n=6 pre- and post-PHx). Timing of the PHx is indicated by the arrow. Error bars denote standard error.
Figure 4C:
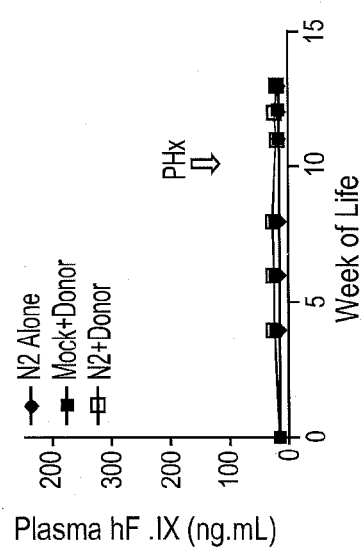
FIG. 4C is a graph showing plasma hFIX levels in wild-type mice following I.P. injection at day 2 of life with either 5e10 v.g. AAV-N2 alone (n=8 pre-PHx, n=4 post-PHx), 5e10 v.g. AAV-N2 and 2.5e11 v.g. AAV-Donor (n=9 pre-PHx, n=5 post-PHx), or 5e10 v.g. AAV-Mock and 2.5e11 v.g. AAV-Donor (n=6 pre-PHx, n=5 post-PHx). Error bars denote standard error.

To confirm stable genomic correction, we performed partial hepatectomies (PHx), which cause extra-chromosomal episomes to be diluted and lost as hepatocytes proliferate during liver regeneration (Nakai et al, (2001), *J. Virol.* 75: 6969-6976) (FIG. 4 A,B). Partial hepatectomies were performed as previously described (Mitchell and Willenbring, (2008) *Nat. Prot.* 3:1167-1170) and all animal procedures were approved by the Children's Hospital of Philadelphia IACUC. Measurement of hFIX levels in N2+Donor-treated mice were unchanged following liver regeneration post-hepatectomy, indicating stable correction. Control mice receiving N2 alone or Mock+Donor continued to average less than 15 ng/mL (FIG. 4A) post-hepatectomy, significantly lower than mice receiving N2+Donor (p≤0.004 at all time points, 2-tailed T-test). To ensure hFIX expression was LP-specific and did not result from random donor integration into the genome, we injected wild-type mice lacking the LP transgene at day 2 of life with AAV-N2 alone (n=8), AAV-Mock+AAV-Donor (n=6), or AAV-N2+AAV-Donor (n=9) (same vector doses as above). Plasma hFIX levels for mice receiving N2 alone, Mock+Donor, and N2+Donor averaged less than 15, 19, and 27 ng/mL, respectively, indicating the majority of hFIX expression in LP mice receiving N2+Donor came from LP-specific correction (FIG. 4C).

Figure 4E:
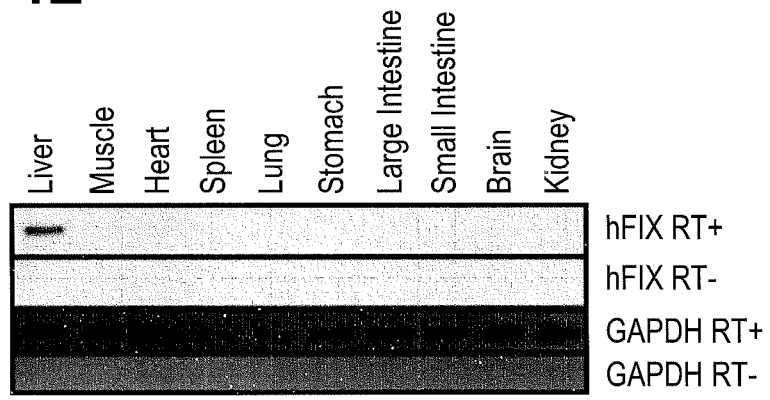
FIG. 4E shows a gel demonstrating liver-specific expression of hFIX RNA as detected by RT-PCR at week 20 of life in an LP/HB mouse receiving I.P. injection at day 2 of life with 5e10 v.g. AAV-N2 and 2.5e11 v.g. AAV-Donor.

To determine if hFIX levels were sufficient to correct the HB phenotype, we injected LP/HB mice at day 2 of life with AAV-N2 alone (n=10), AAV-Mock+AAV-Donor (n=9), or AAV-N2+AAV-Donor (n=9) (same vector doses as above). Plasma hFIX levels for mice receiving N2 alone again averaged less than 15 ng/mL. Mice receiving Mock+Donor averaged less than 25 ng/mL, and mice receiving N2+Donor had significantly higher hFIX levels (p≤0.04 at all time points compared to Mock+Donor, 2-tailed T-test), averaging 166-354 ng/mL (3-7% of normal circulating levels) (FIG. 4D). We confirmed liver-specific hFIX expression by RT-PCR for hFIX mRNA (FIG. 4E). RNA from frozen mouse tissue was isolated using the RNeasy kit (Qiagen) and the RNase-free DNase kit (Qiagen). cDNA synthesis was performed using the iSCRIPT kit (Bio-Rad). RT-PCR for hFIX transcript was performed using primers hFIX Gen1 For (ACCAGCAGT-GCCATTTCCA, SEQ ID NO:25) and hFIX Gen1 Rev (GAATTGACCTGGTTTGGCATCT, SEQ ID NO:26)

Figure 4F:
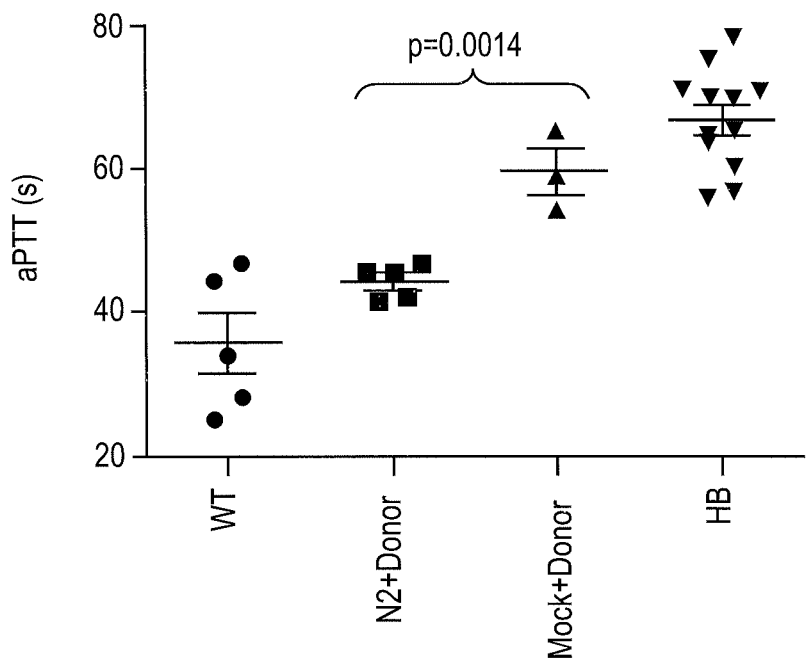
FIG. 4F is a graph showing the time to clot formation as assayed by the activated partial thromboplastin time (aPTT) assay at week 14 of life of mice receiving LP injection at day 2 of life with 5e10 v.g. AAV-N2 and 2.5e11 v.g. AAV-Donor (n=5), or 5e10 v.g. AAV-Mock and 2.5e11 v.g. AAV-Donor (n=3) (p-value from 2-tailed Student's t-test). aPTTs of wild-type (WT) and hemophilia B (HB) mice are shown for comparison.

To assay whether the HB phenotype was corrected, we measured activated partial thromboplastin time (aPTT), a measure of kinetics of fibrin clot formation that is markedly prolonged in hemophilia. aPTT was performed by mixing sample plasma 1:1:1 with pooled HB human plasma and aPTT reagent. Clot formation was initiated by addition of 25 mM calcium chloride. Plasma for aPTT was obtained by tail bleeding 9:1 into sodium citrate. The average aPTTs for wild-type mice (n=5) and HB mice (n=12) were 36 seconds and 67 seconds, respectively (FIG. 4F). Mice receiving Mock+Donor (n=3) averaged 60 seconds, while mice receiving N2+Donor (n=5) had a significantly shortened aPTT, averaging 44 seconds (p=0.0014 compared to Mock+Donor, 2-tailed T-test) (FIG. 4F).

Example 5

In Vivo Co-Delivery of Engineered Nucleases and Donor in Adult Animals

Figure 5A:
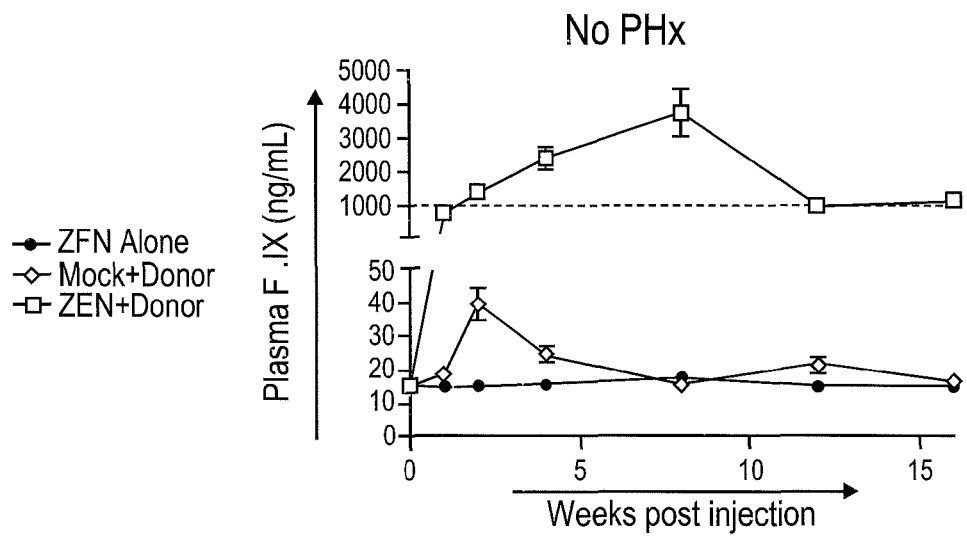
FIG. 5A is a graph showing the plasma hFIX levels in adult LP mice following I.V. injection at 6 weeks of age with either $1e^{11}$ v.g./mouse AAV-N2 alone ('ZFN alone'), $1e^{11}$ v.g./mouse AAV-N2 and 5.5e11 v.g./mouse AAV-Donor ('ZFN+Donor'), or $1e^{11}$ v.g./mouse AAV-Mock and 5.5e11 v.g. AAV-Donor ('Mock+Donor'). The data depicted is representative of 3 experiments with approximately 20 mice per group. In these experiments, the wild type hF.IX levels were approximately 1000 ng/mL.
Figure 5B:
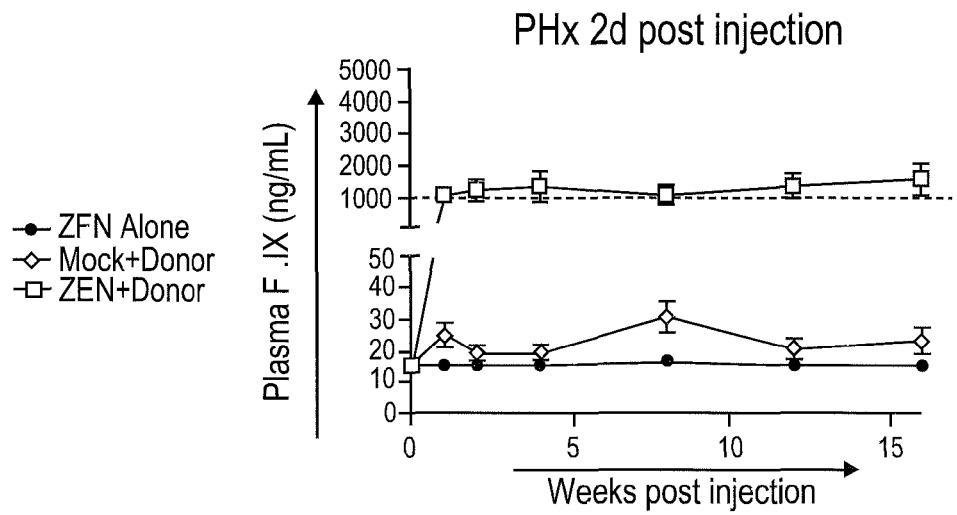
FIG. 5B is a graph showing the plasma hFIX levels in adult LP mice following I.V. injection at 6 weeks of age with either $1e^{11}$ v.g./mouse AAV-N2 alone ('ZFN alone'), $1e^{11}$ v.g./mouse AAV-N2 and 5.5e11 v.g./mouse AAV-Donor ('ZFN+Donor'), or $1e^{11}$ v.g./mouse AAV-Mock and 5.5e11 v.g. AAV-Donor ('Mock+Donor'). Two days following injection, the groups in FIG. 5B were given a partial hepatectomy. The data depicted is representative of 3 experiments with approximately 20 mice per group. In these experiments, the wild type hF.IX levels were approximately 1000 ng/mL. The data demonstrate that hF.IX expression is stable when given to adult mice with or without a follow on partial hepatectomy, and that it is possible to perform genome editing in adult animals.

Adult animals were then subjected to genome editing at the human F.IX LP as described above for the neonates. Adult LP mice were treated by I.V. injection at 6 weeks with either $1e^{11}$ v.g./mouse AAV-N2 alone ('ZFN alone'), $1e^{11}$ v.g./mouse AAV-N2 and 5.5e11 v.g./mouse AAV-Donor ('ZFN+Donor'), or $1e^{11}$ v.g./mouse AAV-Mock and 5.5e11 v.g. AAV-Donor ('Mock+Donor'). The data depicted in FIG. 5A is representative of 3 experiments with approximately 20 mice per group. In these experiments, the wild type hF.IX levels were approximately 1000 ng/mL. Similarly, FIG. 5B is a graph showing the plasma hFIX levels in adult LP mice following I.V. injection at 6 weeks of age with either $1e^{11}$ v.g./mouse AAV-N2 alone ('ZFN alone'), $1e^{11}$ v.g./mouse AAV-N2 and 5.5e11 v.g./mouse AAV-Donor ('ZFN+Donor'), or $1e^{11}$ v.g./mouse AAV-Mock and 5.5e11 v.g. AAV-Donor ('Mock+Donor'). Two days following injection, the groups in FIG. 5B were given a partial hepatectomy. The data depicted is representative of 3 experiments with approximately 20 mice per group. In these experiments, the wild type hF.IX levels were approximately 1000 ng/mL. The data demonstrate that hF.IX expression is stable when given to adult mice with or without a follow on partial hepatectomy, and that it is possible to perform genome editing in adult animals.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A protein comprising an engineered zinc finger protein DNA-binding domain that binds to a target site in an endogenous Factor IX (FIX) gene, wherein the DNA-binding domain comprises four or five zinc finger recognition regions ordered F1 to F4 or F1 to F5 from N-terminus to C-terminus, and wherein
   (i) when the DNA-binding domain comprises five zinc finger recognition regions, F1 to F5 comprise the following amino acid sequences:

F1: QSGDLTR    (SEQ ID NO: 4)

F2: RSDVLSE    (SEQ ID NO: 5)

F3: DRSNRIK    (SEQ ID NO: 6)

F4: RSDNLSE    (SEQ ID NO: 7)

F5: QNATRIN,   (SEQ ID NO: 8)

wherein the DNA-binding domain binds to the target site shown in SEQ ID NO:3; and
   (ii) when the DNA-binding domain comprises four zinc finger recognition regions, F1 to F4 comprise the following amino acid sequences:

F1: RSDSLSV    (SEQ ID NO: 10)

F2: TSGHLSR    (SEQ ID NO: 11)

F3: RSDHLSQ    (SEQ ID NO: 12)

F4: HASTRHC,   (SEQ ID NO: 13)

wherein the DNA-binding domain binds to the target site shown in SEQ ID NO:9.

2. The protein according to claim 1, further comprising a cleavage domain or cleavage half-domain.

3. The protein of claim 2, wherein the cleavage half-domain is a wild-type or engineered FokI cleavage half-domain.

4. A polynucleotide encoding the protein of claim 1.

5. A gene delivery vector comprising a polynucleotide according to claim 4.

6. An isolated cell comprising the protein of claim 1.

7. An isolated cell comprising the polynucleotide of claim 4.

8. A method of integrating an exogenous sequence into an endogenous FIX gene in a cell, the method comprising:
   expressing at least one polynucleotide according to claim 4 in the cell such that the exogenous sequence is integrated into the endogenous FIX gene.

9. A cell made by the method of claim 8.

10. The cell of claim 9, wherein the cell is a hepatic cell or a stem cell.

11. The cell of claim 10, wherein the stem cell is selected from the group consisting of an embryonic stem cell (ESC), an induced pluripotent stem cell (iPSC), a CD34+ hematopoietic stem cell and a hepatic stem cell.

* * * * *